(12) United States Patent
Cravens

(10) Patent No.: US 9,949,857 B2
(45) Date of Patent: Apr. 24, 2018

(54) KNEE ADJUSTMENT DEVICE

(71) Applicant: Dean Leroy Cravens, Belleville, IL (US)

(72) Inventor: Dean Leroy Cravens, Belleville, IL (US)

( * ) Notice: Subject to any disclaimer, the term of this patent is extended or adjusted under 35 U.S.C. 154(b) by 128 days.

(21) Appl. No.: 14/822,733

(22) Filed: Aug. 10, 2015

(65) Prior Publication Data

US 2016/0184163 A1    Jun. 30, 2016

Related U.S. Application Data

(60) Provisional application No. 62/035,396, filed on Aug. 9, 2014.

(51) Int. Cl.
*A61F 5/00* (2006.01)
*A61F 5/01* (2006.01)

(52) U.S. Cl.
CPC .................. *A61F 5/0104* (2013.01)

(58) Field of Classification Search
CPC .. A61F 5/04; A61F 5/06; A61F 5/0123; A61F 2005/0174
USPC ...................................... 602/25–26
See application file for complete search history.

(56) References Cited

U.S. PATENT DOCUMENTS

| | | | | |
|---|---|---|---|---|
| 3,992,004 A | * | 11/1976 | Feron ................. | A63B 21/0552 482/128 |
| 5,658,244 A | * | 8/1997 | Townsend ............ | A61F 5/0123 602/23 |
| 7,291,119 B1 | * | 11/2007 | de Guise ............... | A61B 5/064 600/595 |
| 2016/0151224 A1 | * | 6/2016 | Ferro ................... | A61G 13/101 128/845 |

* cited by examiner

*Primary Examiner* — Kristen Matter

(57) ABSTRACT

A device for adjusting the knee joint. The invention is configured to be a standalone device used by individuals on any flat surface. No power is required, pressure is applied manually. The invention is made to be easily adjustable, configurable, assembled, and transportable.

5 Claims, 3 Drawing Sheets

KNEE ADJUSTMENT DEVICE

TECHNICAL FIELD OF THE INVENTION

This device is closely related to a kinesitherapy instrument or brace. The Knee Adjustment Device provides manual adjustment to move the knee joint to lesson pain of the joint and associated soft tissue.

BACKGROUND OF INVENTION

The human knee joins the femur and tibia bones, is controlled by ligaments/muscles/bands, and cushioned by cartilage. Contact between the femur and the tibia occurs across the cartilage with compartments or spaces around the knee. The medial compartment is on the inside of the knee and the lateral compartment is on the outside of the knee. A healthy knee joint has an even distribution of pressure across the medial and lateral areas of the knee joint. Loss or damage of the cartilage causes the bones to rub together causing inflammation and pain that leads to osteoarthritis or the degeneration of the bones. Osteoarthritis, which may occur in any of the compartments of the knee joint, occurs predominately in the medial or lateral compartments. This degeneration and onslaught of osteoarthritis will result in the knee joint slowly changing in an attempt to relieve the pain and discomfort. With the advancement of the disease, the space between the femur and tibia decreases. The problem may progress to the extent that the space is eliminated and the femur contacts the tibia. In those circumstances, erosion of the tibia may result. This mechanical change causes an alteration in the alignment of the knee and results in the knee joint bowing usually to the lateral or outside of the knee. Also with the pain and onset of disease there is a change in the normal angle between the femur and tibia. A further complication is the development or worsening of slackness in the tendons, ligaments, bands and muscles on one side of the knee and the tendons, ligaments, bands, and muscles become stretched to their limits on the bowed or opposite side of the knee. This then causes pain in both the affected area and bowed side of the knee which is created by the body in an attempt to escape the pain. The pain in the hamstring and quadriceps muscles and the stretching (burning pain) of the ligaments ultimately causes the pain level to be too great on both sides of the knee for an individual to continue to tolerate the pain leaving them currently with only the option of total knee replacement to relieve the pain. In a total knee replacement the complete knee joint is cut out and replaced with an artificial device requiring the cutting and removing of the bones and reattaching the muscles tendons, bands, and ligaments to the artificial device. The total knee replacement process is very expensive, extremely invasive, and requires long periods of rehabilitation. The knee adjustment device can adjust the knee joint so as to create the space between the bones and relieve the stress on the muscles, tendons, and ligaments relieving pain on both sides of the knee. The alleviation of the pain and discomfort allows the individual to move the knee joint in a more normal fashion again. Prior to this device knee pain was treated with drugs or braces; both of which treat symptoms of the problem with neither addressing the actual underlying problems of the joint cartilage deterioration, the space in the knee joint decreasing, and bone on bone contact.

BRIEF SUMMARY OF THE INVENTION

This knee adjustment device addresses the problems associated with the bowing of the leg at the knee joint, knee pain and the onslaught of osteoarthritis by straightening, realigning, and stretching the knee joint to create the space required to alleviate the rubbing of the bones and stretching of the support soft tissue. The adjustment removes bowing from the knee, straightens the knee joint, creates space between the knee bones, and relieves stressing and straining of the muscles, tendons and ligaments. The knee adjustment device applies pressure to one side of the knee while holding the upper and lower leg in place so the knee joint is manipulated to create better spacing and subsequent relief from pain and discomfort. The process allows the knee to be put into a more natural state of alignment, creating a more in-line walking structure. This device can straighten the leg to create a better walking gait, and to help eliminate pain and discomfort in other areas of the body to include but not be limited to: ankle, hip, heel, calf, foot, and back. The leg is placed in the knee adjustment device between the pressure plate and the vertical extensions of the lateral bracing arms with the outside of the knee pressed against the pressure plate and leg lying flat on the floor across the lateral bracing arms. The two lateral bracing arms are then slid through the base bar until they are against the inner thigh and calf/shin. The two ring pins are then placed through the base bar and lateral bracing arms in the closest adjustment hole on each of the two lateral bracing arms. The adjusting knob is then turned clockwise to extend the pressure plate further from the pressure plate stabilizing post applying pressure to the outside of the knee. This will push the leg against the vertical extensions of the lateral bracing arms which will hold the upper and lower portions of the leg stationary while the knee joint is allowed to be moved laterally (inward) toward the inside of leg. The Knee Adjustment Device is also known as Leg Adjustment Device, Leg Straightener, and Debowlegger.

DETAILED DESCRIPTION OF THE INVENTION

Figure 1:
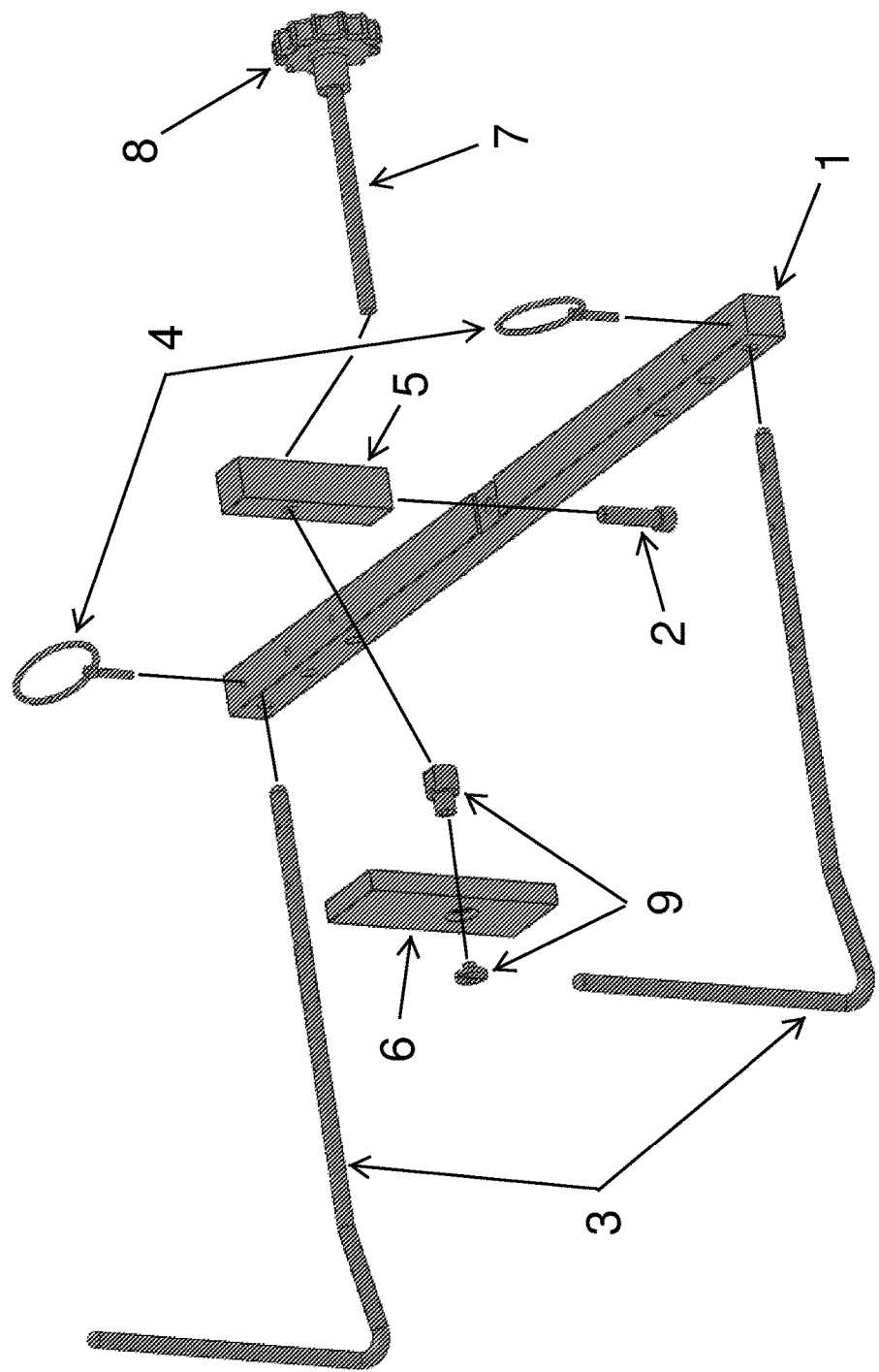
FIG. 1—Illustrates an exploded view of Knee Adjustment Device
Figure 2:
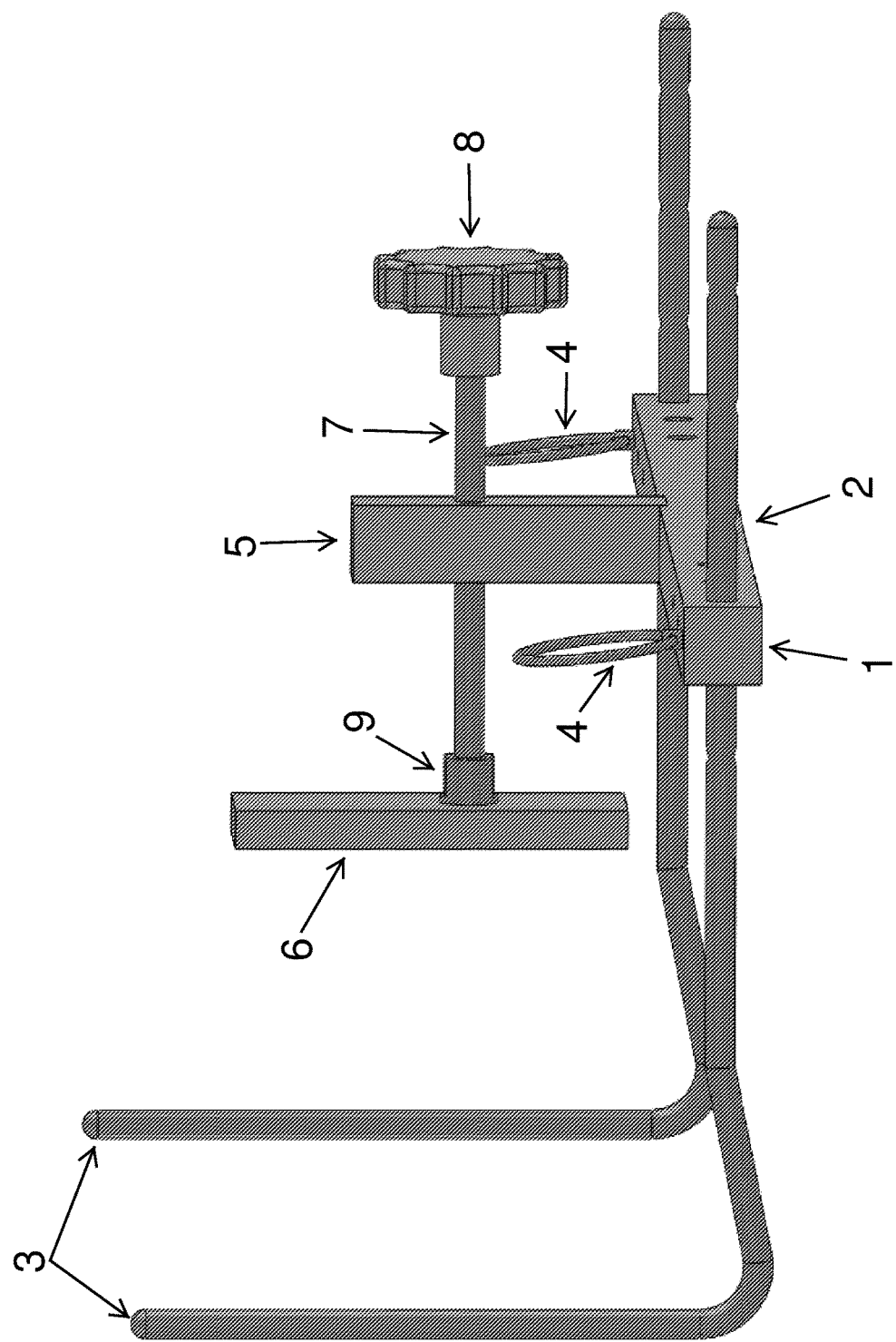
FIG. 2—Illustrates a side view of assembled Knee Adjustment Device
Figure 3:
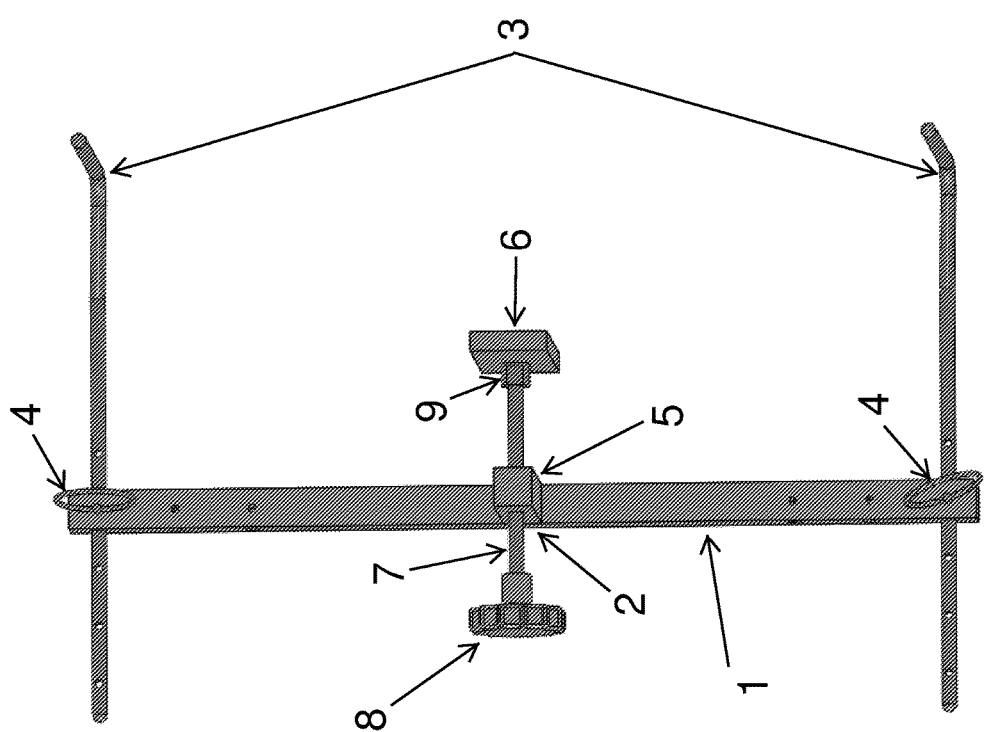
FIG. 3—Illustrates a top view of assembled Knee Adjustment Device

The knee adjustment device, as depicted in FIG. 1, consists of a base bar (1) with adjustment holes; securing bolt(s) (2); two lateral bracing arms (3) with adjustment holes; two ring pins (4); pressure plate stabilizing post (5); pressure plate (6); adjustment bolt (7); adjusting knob (8); and rotating joint coupling (9). The knee adjustment device is adjustable to different widths and lengths of legs with no added components. This one device can fit most individuals.
Description of the Parts:
  Base bar (1) stabilizes the knee adjustment device on the pressure side. The base bar has adjustment holes through which lateral bracing arms slide through for adjusting width and length of the device. This allows it to conform to the size of the individual's leg.
  Securing bolt(s) (2) are bolt(s) inserted through the bottom of the base bar and into the pressure plate stabilizing post to securing the pressure plate, thus stabilizing the post to the base bar.
  Lateral bracing arms (3) are adjustable for the length and width of the upper and lower portion of the leg independently and pass through the base bar with adjustment holes which line up with holes along the base bar. The arms are made of a rigid material to hold the leg in place not allowing lateral movement of the lower and upper leg during the application of pressure to the knee. The vertical extensions of both bracing arms are positioned on the same side of the leg to allow leverage to be applied while the leg is stabilized.

Ring pins (4) are used to set the width and length of the lateral bracing arms. The two ring pins are pushed through the base bar and lateral bracing arms, locking in the width and length of the device. The ring pins can also be used to relieve the pressure on the knee following completion of the adjustment period or for emergency quick release of pressure.

Pressure unit assembly:

Pressure plate stabilizing post (5) is made of a rigid material and is used to brace the pressure plate to allow tension to be applied to the knee joint without change in pressure point location. The pressure plate stabilizing post is bolted to the base bar with two bolts allowing for easy assembly and disassembly.

Pressure plate (6) is a flat piece of metal with a soft material attached for a soft face used to apply pressure to the knee joint. The pressure plate is attached to the device by a bolt attached through the pressure plate stabilizing post. The pressure plate can have a marked adjustment measurement pin attached so the user can determine the level of pressure applied during each session.

Adjustment bolt (7) is threaded bolt screwed through the pressure plate stabilizing post and attached to the pressure plate with a rotating coupling joint to allow for increasing and decreasing of the lateral pressure on the knee without changing the horizontal or vertical positioning of the pressure plate.

Adjusting Knob (8) is an oversized plastic bolt cap attached to one end of the adjustment bolt to allow the individual to manually turn the adjustment bolt to move the pressure plate to apply or relieve pressure to the knee as required.

Rotating joint coupling (9) attaches the adjustment bolt to the pressure plate allowing the bolt to rotate without rotating the pressure plate.

This device can take on many shapes and sizes as long as it provides for upper and lower leg support (bracing) and applies lateral pressure to the proper location. Even though the drawings show a square shaped base bar with rounded tube shaped lateral bracing arms, rectangular shaped pressure plate, and rectangular shaped pressure plate stabilizing post each of these parts could take on any shape or size as long as the pressure and bracing are applied to the proper areas. This device could be made out of any material that is rigid enough to with stand the pressure applied to the knee without bending or breaking. This would include but not be limited to plastics, wood, metals, and concrete. The length and size of the adjusting bolt can be any size strong enough and long enough to apply the pressure to the appropriate knee location and not slip or break. The adjusting knob can be made of any material that can be attached to the bolt and can be used to adjust the bolt with ease to include but not be limited to plastics, rubber, wood, and metal. The pressure unit while depicted using the bolt style adjustment could use but not be limited to a ratcheting device, or lever style. The ring pins can be any type of pin and made of any type of material but should be of the size and type that allows support and quick release in case of emergency. The ring pins can be any thickness and length, as long as they can with stand the pressure of the leg on the lateral bracing arms without bending or breaking. The securing bolt(s) can be any length and any number as long as they can withstand the stress the pressure plate applies to the pressure plate stabilizing plate. This device is easily assembled and disassembled to allow for easy transportation, shipping, and use while on travel.

What is claimed is:

1. A knee adjustment device comprising:
   a base bar;
   a pair of lateral bracing arms each having a vertical extension angled perpendicular to the base bar, the vertical extensions configured to be positioned on a user's knee on a same side of the knee with one of the pair of lateral bracing arms placed on a lower leg of the user, the lateral bracing arms being independently adjustable;
   a pressure plate configured to abut the user's knee on a side opposite from the side with the vertical extensions positioned thereon, the pressure plate configured to apply lateral pressure to the knee towards the vertical extensions at a pressure point;
   a pressure plate stabilizing post mounted to the base bar and configured to allow the pressure plate to be laterally adjusted without changing the pressure point;
   an adjustment bolt comprising an adjustment knob, the adjustment bolt being threaded through the pressure plate stabilizing post and connected to the pressure plate via a rotating coupling joint, the adjustment bolt configured to increase and decrease the lateral pressure applied to the knee through movement of the pressure plate without changing a vertical or horizontal positioning of the pressure plate; and
   ring pins placed through the base bar and each lateral bracing arm, the ring pins configured to lock the lateral bracing arms in a desired position and allow for a quick release of the lateral pressure applied to the knee.

2. The knee adjustment device of claim 1, wherein the base bar and lateral bracing arms each include holes for receiving the ring pins to allow for locking the lateral bracing arms in the desired position.

3. The knee adjustment device of claim 1, wherein the rotating coupling joint on the pressure plate allows for the adjustment bolt to be rotated without rotating the pressure plate.

4. The knee adjustment device of claim 1, wherein the base bar is comprised of a rigid piece of material.

5. The knee adjustment device of claim 1, wherein the lateral bracing arms are comprised of a rigid piece of material.

* * * * *